United States Patent [19]
Brändström et al.

[11] Patent Number: 4,725,691
[45] Date of Patent: Feb. 16, 1988

[54] 2-[8-QUINOLINYL]-SULPHINYL-1H-BENZIMIDAZOLE

[75] Inventors: Arne E. Brändström, Gothenburg; Per L. Lindberg, Askim; Björn Wallmark, Mölnlycke, all of Sweden

[73] Assignee: Aktiebolaget Hassle, Molndal, Sweden

[21] Appl. No.: 913,689

[22] Filed: Sep. 30, 1986

Related U.S. Application Data

[62] Division of Ser. No. 739,425, May 30, 1985, Pat. No. 4,636,499.

[30] Foreign Application Priority Data

Jun. 13, 1984 [SE] Sweden ............... 8403179

[51] Int. Cl.⁴ .......................... C07D 401/12
[52] U.S. Cl. .................... 546/172
[58] Field of Search ............... 546/172

[56] References Cited

U.S. PATENT DOCUMENTS 4,359,465 11/1982 Ruwart ............... 514/338

Primary Examiner—Jane T. Fan
Attorney, Agent, or Firm—Brumbaugh, Graves, Donohue & Raymond

[57] ABSTRACT

Novel compounds of the formula IIIa

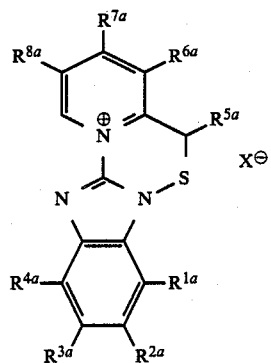

IIIa wherein $R^{1a}$, $R^{2a}$, $R^{3a}$ and $R^{4a}$ are the same or different and are hydrogen, an alkyl, alkoxy optionally completely or predominantly substituted by fluorine or chlorine, halogen, —CN, —CF₃, —NO₂, —COR, —COOR, aryl, aryloxy or arylalkoxy group, or adjacent groups $R^{1a}$, $R^{2a}$, $R^{3a}$ and $R^{4a}$ together with the adjacent carbon atoms in the benzimidazole ring form a 5-, 6- or 7-membered monocyclic ring or a 9-, 10- or 11-membered bicyclic ring, which rings may be saturated or unsaturated and may contain 0–3 heteroatoms selected from N and O and which rings may be optionally substituted with 1–4 substitutents selected from alkyl groups with 1–3 carbon atoms, halogen preferably F or Cl, alkylene radicals containing 4–5 carbon atoms giving spiro compounds, or two or four of these substituents together form one or two oxy groups

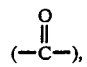

whereby if $R^{1a}$, $R^{2a}$, $R^{3a}$ and $R^{4a}$ together with the adjacent carbon atoms in the benzimidazole ring form two rings they may be condensed with each other, $R^{5a}$ is hydrogen or an alkyl group, $R^{6a}$ is hydrogen or an alkyl group or $R^{5a}$ and $R^{6a}$ are joined together to form an alkylene chain, $R^{7a}$ is hydrogen, an alkyl, alkoxy, alkenyloxy or alkynyloxy group, $R^{8a}$ is hydrogen or an alkyl group, or $R^{6a}$ and $R^{7a}$, or $R^{7a}$ and $R^{8a}$ together with the adjacent carbon atoms in the pyridinium ring form a ring wherein the part constituted by $R^{6a}$ and $R^{7a}$ or $R^{7a}$ and $R^{8a}$, is —CH=CH—CH=CH—, —O—(CH₂)ₚ—, —CH₂(CH₂)ₚ—, —O—CH=CH—, —NH—CH=CH—,

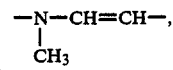

or —S—(CH₂)ₚ—, wherein p is 2, 3 or 4 and the O, S and N atoms always are attached to position 3 in the compound IIIa, R is a alkyl, cycloalkyl, aryl or arylalkyl group, and X⁻ is a pharmaceutically acceptable anion, process for preparation thereof, pharmaceutical compositions containing such compounds and their use in medicine.

1 Claim, No Drawings

2-[8-QUINOLINYL]-SULPHINYL-1H-BENZIMIDAZOLE

This application is a division of application Ser. No. 739,425, filed on May 30, 1985 now U.S. Pat. No. 4,636,499 issued 1/13/87.

FIELD OF THE INVENTION

The present invention is related to new sulphenamide salts having valuable therapeutic properties especially in affecting gastric acid secretion and providing gastrointestinal cytoprotective effect in mammals, including man, as well as processes for the preparation of the new compounds, pharmaceutical compositions comprising them and a method of affecting gastric acid secretion and providing gastrointestinal cytoprotective effect when using them.

BACKGROUND OF THE INVENTION

From e.g. EP-A1-0 005 129 sulphoxides of the benzimidazole type with the general formula I

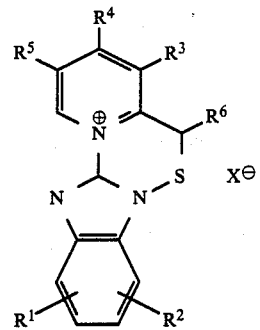

in which $R^1$ and $R^2$ are the same or different and are hydrogen, alkyl, halogen, methoxycarbonyl, ethoxycarbonyl, alkoxy, or alkanoyl in any position, $R^6$ is hydrogen, methyl or ethyl, $R^3$, $R^4$ and $R^5$ are the same or different and are each hydrogen, methyl, methoxy, ethoxy, methoxyethoxy or ethoxyethoxy, whereby $R^3$, $R^4$ and $R^5$ are not all hydrogen, and whereby when two of $R^3$, $R^4$ and $R^5$ are hydrogen, the third of $R^3$, $R^4$ and $R^5$ is not methyl, as well as pharmaceutically acceptable salts thereof are known. The compounds with the general formula I can be used in the treatment of gastrointestinal diseases.

The compounds are known to inhibit gastric acid secretion and have also a gastric cytoprotective effect. Because of their antisecretory effect they may be used in the treatment of peptic ulcer.

The antisecretory activity of the substituted benzimidazoles with the general formula I has been found to be mediated by inhibition of the gastric $H^+,K^+$-ATPase, the enzyme responsible for the pumping of protons into the stomach. This enzyme is localized in the parietal cells in the gastric mucosa.

The in vivo inhibiting effect of the compounds with the general formula I is not, however, exerted by the compounds as such but by one or more degradation products.

OUTLINE OF THE INVENTION

According to the present invention it has now surprisingly been found that the above mentioned degradation reaction of the sulphoxides with the general formula I is a complicated transformation reaction to the new sulphenamides with the general formula III

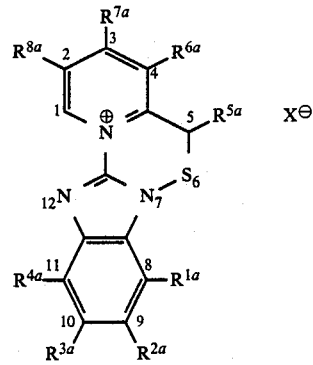

wherein $R^1$, $R^2$, $R^3$, $R^4$, $R^5$ and $R^6$ have the same meaning as given above and $X^-$ is a pharmaceutically acceptable anion.

Compounds of the invention are compounds of the general formula IIIa

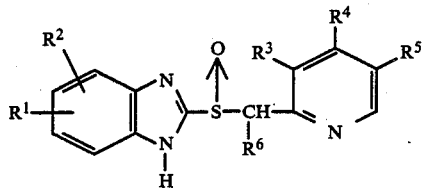

wherein $R^{1a}$, $R^{2a}$, $R^{3a}$ and $R^{4a}$ are the same or different and are hydrogen an alkyl, alkoxy, optionally completely or predominantly substituted by fluorine or chlorine, halogen, —CN, —CF$_3$, —NO$_2$, —COR, —COOR, aryl, aryloxy or arylalkoxy group, or adjacent groups $R^{1a}$, $R^{2a}$, $R^{3a}$ and $R^{4a}$ together with the adjacent carbon atoms in the benzimidazole ring form a 5-, 6- or 7-membered monocyclic ring or a 9-, 10- or 11-membered bicyclic ring, which rings may be saturated or unsaturated and may contain 0-3 hetero atoms selected from N and O and which rings may be optionally substituted with 1-4 substituents selected from alkyl groups with 1-3 carbon atoms, halogen preferably F or Cl, alkylene radicals containing 4-5 carbon atoms giving spiro compounds, or two or four of these substituents together form one or two oxy groups

whereby if $R^{1a}$, $R^{2a}$, $R^{3a}$ and $R^{4a}$ together with the adjacent carbon atoms in the benzimidazole ring form two rings they may be condensed with each other, $R^{5a}$ is hydrogen or an alkyl group, $R^{6a}$ is hydrogen or an alkyl group or $R^{5a}$ and $R^{6a}$ are joined together to form an alkenylene chain, $R^{7a}$ is hydrogen, an alkyl, alkoxy, alkenyloxy or alkynyloxy group, $R^{8a}$ is hydrogen or an alkyl group, or $R^{6a}$ and $R^{7a}$, or $R^{7a}$ and $R^{8a}$ together with the adjacent carbon atoms in the pyridinium ring form a ring wherein the part constituted by $R^{6a}$ and $R^{7a}$ or $R^{7a}$ and $R^{8a}$, is —CH=CH—CH=CH—, —O—(CH$_2$)$_p$—, —CH$_2$(CH$_2$)$_p$—O—CH=CH—, —NH—CH=CH—,

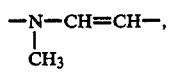

or —S—(CH$_2$)$_p$—, wherein p is 2, 3 or 4 and the O, S and N atoms always are attached to position 3 in the compound IIIa, R is an alkyl, cycloalkyl, aryl or arylalkyl group, and X$^-$ is a pharmaceutically acceptable anion e.g. Cl$^-$, Br$^-$, I$^-$, BF$_4^-$, PF$_6^-$ or AuCl$_4^-$.

R$^{1a}$, R$^{2a}$, R$^{3a}$, R$^{4a}$, R$^{5a}$, R$^{6a}$, R$^{7a}$, R$^{8a}$ and R representing an alkyl group is preferably a lower alkyl group having 1-7 carbon atoms, e.g. methyl, ethyl, n-propyl, isopropyl, n-butyl or isobutyl.

R$^{1a}$, R$^{2a}$, R$^{3a}$, R$^{4a}$ and R$^{7a}$ representing an alkoxy group is preferably a lower alkoxy group having 1-7 carbon atoms, expecially preferred 1-3 carbon atoms e.g. methoxy, ethoxy, n-propoxy or isopropoxy.

R$^{1a}$, R$^{2a}$, R$^{3a}$ and R$^{4a}$ representing a halogen is chloro, bromo, fluoro or iodo.

R$^{1a}$, R$^{2a}$, R$^{3a}$, R$^{4a}$ and R representing an aryl has preferably up to 10 carbon atoms, especially preferred up to 6 carbon atoms e.g. phenyl.

R$^{1a}$, R$^{2a}$, R$^{3a}$ and R$^{4a}$ representing an aryloxy grop has preferably up to 10 carbon atoms, especially preferred up to 6 carbon atoms, e.g. phenoxy.

R$^{1a}$, R$^{2a}$, R$^{3a}$ and R$^{4a}$ representing an arylalkoxy group and R representing an arylalkyl group, have preferably up to 10 carbon atoms in the aryl group and 1-7 carbon atoms in the alkoxy group or the alkyl group, respectively, especially preferred is a group having up to 6 carbon atoms in the aryl group and 1-3 carbon atoms in the alkoxy group or the alkyl group, respectively, e.g. phenylmethoxy, and phenylmethyl.

R$^{5a}$ and R$^{6a}$ representing an alkenylene chain having 3 carbon atoms, thus forming a quinoline ring is especially preferred.

R$^{7a}$ representing an alkenyloxy or alkynyloxy group has preferably 2-5 carbon atoms, especially preferred 3 carbon atoms.

R representing a cycloalkyl group has preferably 3-10 carbon atoms, especially preferred 3 carbon atoms.

A preferred group of compounds with the general formula IIIa are those wherein at least two of R$^{1a}$, R$^{2a}$, R$^{3a}$ and R$^{4a}$ are hydrogen and one or two of the other is a methyl group, R$^{5a}$ is hydrogen, at least one of R$^{6a}$ and R$^{8a}$ is a methyl group and R$^{7a}$ is hydrogen or a methoxy group.

Especially preferred according to the invention is the isomeric mixture of 2,4-dimethyl-3,9-dimethoxy-5H-pyrido[1',2':4,5][1,2,4]thiadiazino[2,3-a]benzimidazol-13-ium tetrafluoroborate and 2,4-dimethyl-3,10-dimethoxy-5H-pyrido[1',2':4,5][1,2,4]thiadiaziazino[2,3-a]benzimidazol-13-ium tetrafluoroborate.

The new compounds with the general formula IIIa according to this invention are potent enzyme inhibitors, primarily inhibitors of the enzyme H$^+$,K$^+$-ATPase. In addition, the new compounds exhibit a gastrointestinal cytoprotective effect. In the form of a suitable pharmaceutical composition, the new compounds are therapeutically useful, primarily in the treatment of gastric disorders, such as gastrointestinal inflammatory diseases, including e.g. gastritis, gastric and duodenal ulcer. They may also be used as gastrointestinal cytoprotecting agents.

Compounds of the general formula IIIa above may be prepared according to the following method

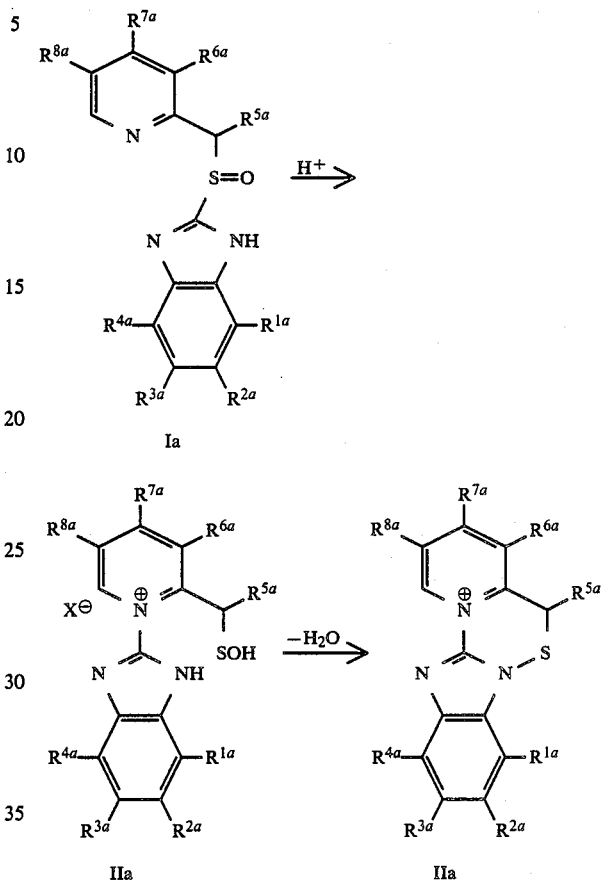

The transformation reaction probably goes via the sulphenic acid IIa, which may also be an in vivo inhibitor, when a sulphoxide with the general formula Ia has been administered. However, the sulphenic acid is probably not an isolable compound. The transformation from the sulphoxide to the sulphenamide goes via two different pathways, namely (a) one acid catalyzed and (b) one non-acid catalyzed pathway. Both pathways, however, give the same sulphenamide, IIIa.

Especially preferred acids for preparation of the compounds with the general formula IIIa are HPF$_6$, HBF$_4$, HAuCl$_4$ and HCl.

The compounds with the general formula Ia, wherein R$^{5a}$ and R$^{6a}$ together form an alkenylene chain are new compounds, which form a part of the invention.

The compounds with the general formula IIa are new compounds, which form a part of the invention.

Method (a)

0.005 mole of a sulphoxide with the general formula Ia is dissolved in 50 ml of 0.2M HCl in CH$_3$OH (1 ml of HCl and 49 ml of CH$_3$OH) at 37° C. and is stirred for 7 minutes. (1 ml of acid HPF$_6$, HBF$_4$ or HAuCl$_4$) is added and the solution is cooled to 10° C. Crystals of the sulphenamide with the general formula IIIa are precipitated, filtered off and dried.

Method (b)

0.005 mole of a sulphoxide with the general formula Ia is dissolved in 50 ml of 0.2M HCl in CH$_3$OH (1 ml of HCl and 49 ml of CH$_3$OH) at 37° C. and is stirred for 7 min. The solution is cooled, whereby a sulphenamide with the general formula IIIa is precipitated as its Cl$^-$-salt. The precipitate is filtered off and dried.

Method (b)

0.01 mole of a sulphoxide with the general formula Ia is dissolved in 100 ml 0.2M methanolic HBF$_4$ (2.5 ml 50% HBF$_4$ and 97.5 ml of CH$_3$OH) at 37° C. and is stirred for 2 min. 50 ml of MeOH is added and the mixture is then stirred for another 3 min at 37° C. The mixture is cooled to 5° C. Crystals of the sulphenamide with the general formula IIIa are precipitated, filtered off and dried.

The invention also relates to pharmaceutical compositions containing the new sulphenamides as active ingredient; to the use of the novel sulphenamides in therapy, especially for providing gastrointestinal cytoprotective effects in mammals and man; to the use of the novel sulphenamides in the prevention and treatment of gastrointestinal inflammatory diseases in mammals and man; to a method for inhibiting gastric acid secretion in mammals and man by administering a compound of the formula IIIa, to a method for the treatment of gastrointestinal inflammatory diseases in mammals and man by administering a compound of the formula IIIa; and to a method for providing gastrointestinal cytoprotective effects mammals and man by administering a compound of the formula IIIa.

For clinical use the compounds of the invention are formulated into pharmaceutical formulations for oral, rectal, parenteral or other mode of administration. The pharmaceutical formulation contains a compound of the invention in combination with a pharmaceutically acceptable carrier. The carrier may be in the form of a solid, semisolid or liquid diluent, or a capsule. These pharmaceutical preparations are a further object of the invention. Usually the amount of active compound is between 0.1–95% by weight of the preparation.

In the preparation of pharmaceutical formulations containing a compound of the present invention in the form of dosage units for oral administration the compound selected may be mixed with a solid, powdered carrier, e.g. calcium phosphate, lactose, saccharose, sorbitol, mannitol, starch, amylopectin, cellulose derivatives or gelatin, as well as with lubricating agents e.g. magnesium stearate, calcium stearate, sodium steryl fumarate and polyethylene glycol waxes. The mixture is then processed into granules or pressed into tablets. The tablets may be film coated by a suitable film-forming material.

Soft gelatine capsules may be prepared with capsules containing a mixture of the active compound or compounds of the invention and a suitable vehicle for soft gelatine capsules. Hard gelatine capsules may also contain the active compound in combination with a solid powdered carrier e.g. lactose, saccharose, sorbitol, mannitol, potato starch, corn starch, amylopectin, cellulose derivatives or gelatine.

The oral dosage forms may be enteric coated. The enteric coating is chosen among pharmaceutically acceptable enteric-coating materials e.g. beeswax, shellac or anionic film-forming polymers such as cellulose acetate phthalate, hydroxypropyl methylcellulose phthalate, partly methyl esterified methacrylic acid polymers and the like, if preferred in combination with a suitable plasticizer. To this coating various dyes may be added in order to distinguish among tablets or granules with different active compounds or with different amounts of the active compound present.

The typical daily dose of the active substance varies within a wide range and will depend on various factors such as for example the individual requirement of each patient, the manner of administration and the disease. In general, oral and parenteral dosages will be in the range of 1 to 400 mg per day of active substance.

EXAMPLE 1A+1B 2,4-Dimethyl-3,9-dimethoxy-5H-pyrido[1',2':4,5][1,2,4]-thiadiazino[2,3-a]benzimidazol-13-ium tetrafluoroborate (1A) and 2,4-Dimethyl-3,10-dimethoxy-5H-pyrido[1',2':4,5][1,2,4]thiadiazino[2,3-a]benzimidazol-13-ium tetrafluoroborate (1B) (isomeric mixture)

Method a

5-Methoxy-2-[[(4-methoxy-3,5-dimethyl-2-pyridinyl)methyl]sulphinyl]-1H-benzimidazole (1.72 g, 0.005 mol) was dissolved in 0.2M methanolic HCl (50 ml) (1 ml conc. HCl and 49 ml CH$_3$OH) and stirred at 37° C. for 7 min. Conc. HBF$_4$ (1 ml) was added and the solution was cooled to 10° C. The desired mixture of the isomeric sulphenamide products was filtered off as a crystalline material and dried. Yield: 1.25 g (60%). NMR. See Table 2.

Method b

5-Methoxy-2-[[(4-methoxy-3,5-dimethyl-2-pyridinyl)methyl]sulphinyl]-1H-benzimidazole (3.45 g, 0.01 mol) was dissolved in 0.2M methanolic HBF$_4$ (100 ml) (2.5 ml 50% HBF$_4$ and 97.5 ml CH$_3$OH) and stirred at 37° C. for 2 min. More methanol (50 ml) was added and the mixture was stirred for another 3 min at 37° C. The mixture was cooled to 5° C., whereupon the desired mixture of isomeric sulphenamide products (1A+1B) precipitated out. The product in the form of an isomeric mixture was filtered off and dried, yielding 3.3 g (79%). NMR: See Table 2.

EXAMPLE 11

3-Methoxy-4,9,10-trimethyl-5H-pyrido[1',2':4,5][1,2,4]-thiadiazino[2,3-a]benzimidazol-13-ium chloride (11)

(Method b)

5,6-Dimethyl-2-[[(4-methoxy-3-methyl-2-pyridinyl)methyl]sulphinyl]-1H-benzimidazole (1.60 g, 0.005 mol) was dissolved in 0.2M methanolic HCl (50 ml) (1 ml conc. HCl and 49 ml CH$_3$OH) and stirred at 37° for 7 min. The solution was cooled and the desired sulphenamide salt precipitated. The product was filtered off and dried, yielding 0.3 g (17%). NMR: See Table 2.

EXAMPLE 12

Benzimidazo[1,2-b]pyrido[1,2,3-de][1,2,3]benzothiadiazin-14-ium, hexafluorophosphate (12)

(Method a)

2-[8-quinolinyl]-sulphinyl-1H-benzimidazole (1.50 g, 0.005 mol) was dissolved in 0.2M methanolic HCl (50 ml) (1 ml conc. HCl and 49 ml CH$_3$OH) and the solution was stirred at 37° for 7 min. Conc. HPF$_6$ (1 ml) was added and the solution was cooled to 10° C. The desired sulphenamide salt was filtered off as a crystalline material and dried. M.p. 199° C.

The starting compound was prepared according to the following method.

Preparation of 2-[8-quinolinyl]-thio-1H-benzimidazole

To 8-mercaptoquinoline hydrochloride (5.00 g, 0.025 mol) in ethanol (250 ml) conc. HCl (2.25 ml) and 2-chlorobenzimidazole (3.86 g, 0.025 mol) were added. The mixture was refluxed overnight. pH was adjusted to 13.0 by addition of 2M NaOH. Part of the solvent was evaporated off. The mixture was poured on ice-water. Filtration and recrystallization from $CH_3CN$ gave the desired product (4.50 g, 65%), m.p. 215° C.

Preparation of 2-[8-quinolinyl]-sulphinyl-1H-benzimidazole m-Chloroperbenzoic acid, 82% (3.42 g, 0.016 mol) dissolved in $CH_2Cl_2$ (100 ml) and cooled to −10° C. was added under stirring to 2-[8-quinolinyl]-thio-1H-benzimidazole (4.50 g, 0.016 mol) dissolved in $CH_2Cl_2$ (150 ml) maintaining the temperature at −5° C. Stirring was continued at −5° C. for 10 min. The $CH_2Cl_2$-solution was washed with $NaHCO_3$ (2.69 g, 0.032 mol) dissolved in water (100 ml). The organic phase was dried ($Na_2SO_4$), filtered and the solvent was evaporated off. $CH_3CN$ was added to the residue and the mixture was warmed under stirring. The precipitate was filtered off and washed with warm $CH_3CN$, giving the desired product (2.40 g, 51%), m.p. 205° C.

TABLE 1

Representative examples of compounds included in the scope of the invention.

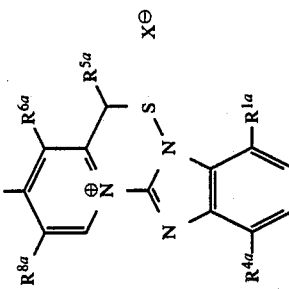

IIIa

| Example No. | $R^{1a}$ | $R^{2a}$ | $R^{3a}$ | $R^{4a}$ | $R^{5a}$ | $R^{6a}$ | $R^{7a}$ | $R^{8a}$ | $X^\ominus$ | Identified by M.p. °C. or NMR |
|---|---|---|---|---|---|---|---|---|---|---|
| 1A  | H    | —OCH₃ | H     | H   | H         | —CH₃        | —OCH₃       | —CH₃ | BF₄   | NMR |
| 1B  | H    | H     | —OCH₃ | H   | H         | —CH₃        | —OCH₃       | —CH₃ | BF₄   | NMR |
| 2A  | H    | —OCH₃ | H     | H   | H         | —CH₃        | —OCH₃       | —CH₃ | PF₆   | NMR |
| 2B  | H    | H     | —OCH₃ | H   | H         | —CH₃        | —OCH₃       | —CH₃ | PF₆   | NMR |
| 3A  | H    | —OCH₃ | H     | H   | H         | —CH₃        | —OCH₃       | —CH₃ | AuCl₄ | NMR |
| 3B  | H    | H     | —OCH₃ | H   | H         | —CH₃        | —OCH₃       | —CH₃ | AuCl₄ | NMR |
| 4   | H    | H     | H     | H   | H         | —CH₃        | —OCH₃       | —CH₃ | AuCl₄ | NMR |
| 5   | H    | —CH₃  | H     | H   | H         | —CH₃        | —OCH₃       | —CH₃ | PF₆   | NMR |
| 6   | H    | H     | —CH₃  | H   | H         | —CH₃        | —OCH₃       | —CH₃ | AuCl₄ | 225 |
| 7A  | H    | —CH₃  | —CH₃  | H   | —CH₃      | H           | H           | H    | BF₄   | NMR |
| 7B  | H    | H     | —CH₃  | H   | —CH₃      | H           | H           | H    | BF₄   | NMR |
| 8   | H    | —CH₃  | —CH₃  | H   | —CH₃      | H           | H           | H    | BF₄   | NMR |
| 9   | H    | —CH₃  | —CH₃  | H   | H         | —CH₃        | —OCH₃       | H    | BF₄   | 187 |
| 10  | H    | —CH₃  | —CH₃  | H   | H         | —CH₃        | —OCH₃       | H    | BF₄   | NMR |
| 11  | H    | —CH₃  | —CH₃  | H   | H         | —CH₃        | H           | H    | Cl    | NMR |
| 12  | H    | H     | —CH₃  | H   | =CH—CH=CH—CH— |         | H           | H    | BF₄   | 199 |
| 13  | H    | —CH₃  | —CH₃  | H   | H         | —CH₃        | —CH₃        | —CH₃ | PF₆   | NMR |
| 14  | H    | H     | H     | —CH₃| H         | —CH₃        | —CH₃        | H    | BF₄   | 215 |
| 15  | H    | H     | —CH₃  | —CH₃| H         | —CH₃        | H           | H    | Cl    | 170 |
| 16  | —CH₃ | —CH₃  | —CH₃  | —CH₃| H         | —CH₃        | —OCH₂CH=CH₂ | —CH₃ | Cl    |     |
| 17  | —CH₃ | —CH₃  | —CH₃  | —CH₃| H         | —CH₃        | —OCH₂CH=CH₂ | —CH₃ | PF₆   |     |
| 18  | H    | —CH₃  | —CH₃  | —CH₃| H         | —CH₃        | —OCH₂CH=CH₂ | —CH₃ | BF₄   |     |
| 19  | —CH₃ | —CH₃  | —CH₃  | H   | H         | —CH₃        | —OCH₃       | —CH₃ | AuCl₄ |     |
| 20  | —CH₃ | —CH₃  | —CH₃  | —CH₃| H         | —CH₃        | —OCH₂CH=CH₂ | —CH₃ | PF₆   |     |
| 21  | H    | —CH₃  | —CH₃  | H   | H         | —CH₃        | —OCH₃       | —CH₃ | BF₄   |     |
| 22  | H    | —CH₃  | —CH₃  | H   | H         | —CH₃        | —OCH₂CH=CH₂ | —CH₃ | AuCl₄ |     |
| 23  | —CH₃ | —CH₃  | —CH₃  | H   | H         | —CH₃        | —OCH₂CH=CH₂ | —CH₃ | Cl    |     |
| 24  | —CH₃ | H     | H     | —CH₃| H         | —CH₃        | —OCH₂CH=CH₂ | —CH₃ | Cl    |     |
| 25  | H    | H     | —CH₃  | —CH₃| H         | —CH₃        | —OCH₂CH=CH₂ | —CH₃ | BF₄   |     |
| 26  | H    | H     | H     | H   | H         | —CH₃        | —OCH₂CH=CH₂ | —CH₃ | AuCl₄ |     |
| 27  | H    | H     | —OCH₃ | H   | H         | —CH₃        | —OCH₂CH=CH₂ | —CH₃ | PF₆   |     |
| 28  | H    | H     | —OCH₃ | H   | H         | —CH₃        | —OCH₂C≡CH   | —CH₃ | Cl    |     |

TABLE 1-continued

Representative examples of compounds included in the scope of the invention.

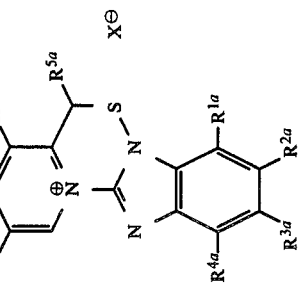

IIIa

| Example No. | $R^{1a}$ | $R^{2a}$ | $R^{3a}$ | $R^{4a}$ | $R^{5a}$ | $R^{6a}$ | $R^{7a}$ | $R^{8a}$ | $X^{\ominus}$ | Identified by M.p. °C. or NMR |
|---|---|---|---|---|---|---|---|---|---|---|
| 29 | H | H | —OCH$_3$ | H | H | —CH$_3$ | —O(CH$_2$)$_3$CH=CH$_2$ | —CH$_3$ | AuCl$_4$ | |
| 30 | H | H | —OCH$_3$ | H | H | —CH$_3$ | —O(CH$_2$)$_3$CH$_3$ | —CH$_3$ | Cl | |
| 31 | H | H | —OCH$_3$ | H | H | —CH$_3$ | —OCH(CH$_3$)$_2$ | —CH$_3$ | PF$_6$ | |
| 32 | H | H | —OCH$_3$ | H | H | —CH$_3$ | —OC(CH$_3$)$_3$ | —CH$_3$ | BF$_4$ | |
| 33 | H | —CH$_3$ | —OCH$_3$ | —CH$_3$ | H | —CH$_3$ | —OCH$_2$CH$_2$CH(CH$_3$)$_2$ | —CH$_3$ | Cl | |
| 34 | H | —CH$_3$ | —OCH$_3$ | —CH$_3$ | H | —CH$_3$ | —CH(CH$_3$)$_2$ | —CH$_3$ | PF$_6$ | |
| 35 | H | H | H | H | H | H | —OCH$_2$CH=CH$_2$ | —CH$_3$ | BF$_4$ | |
| 36 | H | H | —O—C$_6$H$_5$ | H | H | —CH$_3$ | —OCH$_3$ | —CH$_3$ | AuCl$_4$ | |
| 37 | H | H | —OCH$_2$CH$_2$—C$_6$H$_5$ | H | H | —CH$_3$ | —OCH$_3$ | —CH$_3$ | PF$_6$ | |
| 38 | H | —CH$_3$ | —COOCH$_3$ | H | H | —CH$_3$ | —OCH$_2$CH=CH$_2$ | —CH$_3$ | BF$_4$ | |
| 39 | H | H | —CH(CH$_3$)$_2$ | H | H | —CH$_3$ | —OCH$_2$CH=CH$_2$ | —CH$_3$ | Cl | |
| 40 | H | H | —C(CH$_3$)$_3$ | H | H | —CH$_3$ | —OCH$_2$CH=CH$_2$ | —CH$_3$ | AuCl$_4$ | |
| 41 | H | —CH$_3$ | —OCH$_3$ | —CH$_3$ | H | —CH$_3$ | —OCH$_3$ | —CH$_3$ | BF$_4$ | |
| 42 | H | —CH$_3$ | —OCH$_3$ | —CH$_3$ | H | —CH$_3$ | —CH$_3$ | H | AuCl$_4$ | |
| 43 | H | —CH$_3$ | —OCH$_3$ | —CH$_3$ | H | —CH$_3$ | —OCH$_3$ | —CH$_3$ | PF$_6$ | |
| 44 | H | —CH$_3$ | —COCH$_3$ | —CH$_3$ | H | —CH$_3$ | H | —CH$_3$ | Cl | |
| 45 | H | —CH$_3$ | —COC$_2$H$_5$ | —CH$_3$ | —CH$_3$ | —CH$_3$ | —OCH$_3$ | —CH$_3$ | AuCl$_4$ | |
| 46 | H | —CH$_3$ | —CH$_3$ | —CH$_3$ | H | —CH$_3$ | —OCH$_3$ | —CH$_3$ | BF$_4$ | |
| 47 | H | —CH$_3$ | —CH$_3$ | —CH$_3$ | H | —CH$_3$ | —CH$_3$ | —CH$_3$ | PF$_6$ | |
| 48 | H | —CH$_3$ | —C$_2$H$_5$ | —CH$_3$ | H | —CH$_3$ | —OCH$_3$ | —CH$_3$ | Cl | |
| 49 | H | —CH$_3$ | —C$_2$H$_5$ | —CH$_3$ | H | —CH$_3$ | —OCH$_3$ | H | PF$_6$ | |

TABLE 1-continued

Representative examples of compounds included in the scope of the invention.

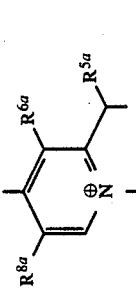   IIIa

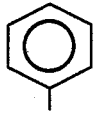

| Example No. | $R^{1a}$ | $R^{2a}$ | $R^{3a}$ | $R^{4a}$ | $R^{5a}$ | $R^{6a}$ | $R^{7a}$ | $R^{8a}$ | $X^\ominus$ | Identified by M.p. °C. or NMR |
|---|---|---|---|---|---|---|---|---|---|---|
| 50 | H | —CH$_3$ | —CH(CH$_3$)$_2$ | —CH$_3$ | H | —CH$_3$ | —OCH$_3$ | —CH$_3$ | BF$_4$ | |
| 51 | H | —CH$_3$ | —CH(CH$_3$)$_2$ | —CH$_3$ | H | —CH$_3$ | —CH$_3$ | —CH$_3$ | AuCl$_4$ | |
| 52 | H | —OCH$_3$ | —Br | —OCH$_3$ | H | —CH$_3$ | —OCH$_3$ | —CH$_3$ | PF$_6$ | |
| 53 | H | —OCH$_3$ | —Br | —OCH$_3$ | H | —CH$_3$ | —CH$_3$ | H | BF$_4$ | |
| 54 | H | —C$_2$H$_5$ | —CN | —C$_2$H$_5$ | H | —CH$_3$ | —OCH$_3$ | H | AuCl$_4$ | |
| 55 | —CH$_3$ | —C$_2$H$_5$ | —CN | —C$_2$H$_5$ | H | —CH$_3$ | —OC$_2$H$_5$ | —CH$_3$ | Cl | |
| 56 | —CH$_3$ | —CH$_3$ | —OCH$_3$ | —CH$_3$ | H | —CH$_3$ | —OCH$_3$ | —CH$_3$ | Cl | |
| 57 | —CH$_3$ | H | —OCH$_3$ | —CH$_3$ | H | —CH$_3$ | —OCH$_3$ | —CH$_3$ | BF$_4$ | |
| 58 | —OCH$_3$ | H | —OCH$_3$ | —Cl | H | —CH$_3$ | —OCH$_3$ | —CH$_3$ | AuCl$_4$ | |
| 59 | H | —Cl | —Cl | H | H | —CH$_3$ | —OCH$_3$ | —CH$_3$ | PF$_6$ | |
| 60 | H | —CH$_3$ | —CH$_3$ | —CH$_3$ | H | H | —OCH$_3$ | —CH$_3$ | Cl | |
| 61 | H | —CH$_3$ | —O(CH$_2$)$_6$CH$_3$ | H | H | —CH$_3$ | —OCH$_3$ | —C$_2$H$_5$ | AuCl$_4$ | |
| 62 | H | H | —C$_2$H$_5$ | H | H | —CH$_3$ | —OCH$_3$ | —CH$_3$ | Cl | |
| 63 | H | H | —OCH$_3$ | H | H | —CH$_3$ | —OCH$_2$CH=CH$_2$ | —CH$_3$ | PF$_6$ | |
| 64 | H | H | —C(CH$_3$)$_3$ | H | H | —CH$_3$ | —O(CH$_2$)$_2$CH(CH$_3$)$_2$ | —CH$_3$ | BF$_4$ | |
| 65 | H | H | —C$_6$H$_5$ (phenyl) | H | H | —CH$_3$ | —OCH$_2$CH=CH$_2$ | —CH$_3$ | Cl | |
| 66 | H | H |  | H | H | —CH$_3$ | —OCH$_3$ | —CH$_3$ | PF$_6$ | |
| 67 | H | H | —NO$_2$ | H | H | —CH$_3$ | —OCH$_3$ | —CH$_3$ | BF$_4$ | |
| 68 | H | H | —Br | H | H | —CH$_3$ | —OCH$_2$CH=CH$_2$ | —CH$_3$ | AuCl$_4$ | |
| 69 | H | —CH$_3$ | —COCH$_3$ (O=) | H | H | H | —OCH$_3$ | —C$_2$H$_5$ | PF$_6$ | |
| 70 | H | —CH$_3$ | —CH$_3$ | —CH$_3$ | H | —CH$_3$ | —CH$_3$ | H | BF$_4$ | |
| 71 | H | —CH$_3$ | —CH$_3$ | —CH$_3$ | H | H | —CH$_3$ | —CH$_3$ | Cl | |

TABLE 1-continued

Representative examples of compounds included in the scope of the invention.

IIIa

| Example No. | $R^{1a}$ | $R^{2a}$ | $R^{3a}$ | $R^{4a}$ | $R^{5a}$ | $R^{6a}$ | $R^{7a}$ | $R^{8a}$ | $X^{\ominus}$ | Identified by M.p. °C. or NMR |
|---|---|---|---|---|---|---|---|---|---|---|
| 72 | H | —CH$_3$ | —CH$_3$ | —CH$_3$ | H | —CH$_3$ | H | —CH$_3$ | AuCl$_4$ | |
| 73 | —CH$_3$ | H | —CH$_3$ | —CH$_3$ | H | —CH$_3$ | —CH$_3$ | H | BF$_4$ | |
| 74 | H | —CH$_3$ | —CN | —CH$_3$ | H | —CH$_3$ | —OC$_2$H$_5$ | —CH$_3$ | AuCl$_4$ | |
| 75 | H | H | —OCH$_3$ | H | H | H | —OCH$_3$ | —C$_2$H$_5$ | PF$_6$ | |
| 76 | H | —CH$_3$ | H | —CH$_3$ | H | H | —OCH$_2$CH=CH$_2$ | —CH$_3$ | Cl | |
| 77 | H | H | —CF$_3$ | H | H | —CH$_3$ | —OCH$_3$ | —CH$_3$ | AuCl$_4$ | |
| 78 | H | H | —NO$_2$ | H | H | —CH$_3$ | —OCH$_3$ | —CH$_3$ | BF$_4$ | |
| 79 | H | H | —Cl | H | H | —CH$_3$ | —OCH$_3$ | —CH$_3$ | PF$_6$ | |
| 80 | H | OCH$_3$ | H | H | H | —CH$_2$CH$_2$CH$_2$O— | | H | PF$_6$ | |
| 81 | H | H | H | H | H | —CH$_2$CH$_2$CH$_2$O— | | H | Cl | |
| 82 | H | OCH$_3$ | H | H | H | —CH$_2$CH$_2$CH$_2$CH$_2$— | | H | BF$_4$ | |
| 83 | H | H | H | H | H | —CH$_2$CH$_2$CH$_2$CH$_2$— | | H | PF$_6$ | |
| 84 | H | OCH$_3$ | H | H | H | —CH$_2$CH$_2$CH$_2$S— | | H | PF$_6$ | |
| 85 | H | H | H | H | H | —CH$_2$CH$_2$CH$_2$CH$_2$— | | H | PF$_6$ | |
| 86 | H | —OCF$_2$CHFO— | | H | H | H | OCH$_3$ | H | PF$_6$ | |
| 87 | H | —OCF$_3$CHFO— | | H | H | CH$_3$ | OCH$_3$ | H | PF$_6$ | |
| 88 | H | —OCF$_2$O— | | H | H | H | OCH$_3$ | H | Br | |
| 89 | H | —OCF$_2$O— | | H | H | CH$_3$ | OCH$_3$ | H | Cl | |
| 90 | H | —OCF$_2$O— | | H | H | H | OCH$_3$ | CH$_3$ | Cl | |
| 91 | H | —OCF$_2$CFClO— | | H | H | CH$_3$ | OCH$_3$ | H | BF$_4$ | |
| 92 | H | —CO⟨△⟩ | H | H | H | CH$_3$ | OCH$_3$ | H | Cl | |
| 93 | H | —CO⟨△⟩ | H | H | H | H | OCH$_3$ | H | I | |

TABLE 1-continued
Representative examples of compounds included in the scope of the invention.

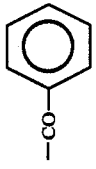

IIIa

| Example No. | $R^{1a}$ | $R^{2a}$ | $R^{3a}$ | $R^{4a}$ | $R^{5a}$ | $R^{6a}$ | $R^{7a}$ | $R^{8a}$ | $X^\ominus$ | Identified by M.p. °C. or NMR |
|---|---|---|---|---|---|---|---|---|---|---|
| 94 | H | —C₆H₄—O— | H | H | H | CH₃ | OCH₃ | H | BF₄ | |
| 95 | H | OCF₃ | H | H | H | CH₃ | OCH₃ | H | PF₆ | |
| 96 | H | OCF₃ | H | H | H | H | OCH₃ | H | Cl | |
| 97 | H | OCF₃ | H | H | H | H | OCH₃ | CH₃ | PF₆ | |
| 98 | H | OCF₃ | H | H | H | CH₃ | OCH₃ | CH₃ | Cl | |
| 99 | H | OCF₂CHF₂ | H | H | H | H | OCH₃ | H | Br | |
| 100 | H | OCF₂CHF₂ | H | H | H | H | OCH₃ | CH₃ | Cl | |
| 101 | H | OCF₂CHF₂ | H | H | H | CH₃ | OCH₃ | H | PF₆ | |
| 102 | H | OCH₂CF₃ | H | H | H | H | OCH₃ | H | PF₆ | |
| 103 | H | OCHF₂ | H | H | H | CH₃ | OCH₃ | H | PF₆ | |
| 104 | H | OCHF₂ | OCHF₂ | H | H | H | OCH₃ | H | PF₆ | |
| 105 | H | OCHF₂ | OCH₃ | H | H | CH₃ | OCH₃ | H | PF₆ | |

Identifying data for the compounds according to the examples 1-5, 7, 8, 10, 11 and 13 are given in the following table 2.

TABLE 2

| Compound according to example | | NMR data (90 MHz) δppm (CD$_3$CN) |
|---|---|---|
| 1A | } isomeric | 2.53(s,3H), 2.63(s,3H), 3.97(s,3H), 4.37(s,3H), |
| 1B | } mixture | 4.90(s,2H), 6.97-7.83(m,3H), 9.30(s,1H) |
| 2A | } isomeric | 2.53(s,3H), 2.63(s,3H), 3.93(s,3H), 4.37(s,3H), |
| 2B | } mixture | 4.90(s,2H), 7.0-7.83(m,3H), 9.30(s,1H) |
| 3A | } isomeric | 2.50(s,3H), 2.60(s,3H), 3.90(s,3H), 4.30(s,3H), |
| 3B | } mixture | 4.83(s,2H), 7.0-7.80(m,3H), 9.30(s,1H) |
| 4 | | 2.50(s,3H), 2.63(s,3H), 4.37(s,3H), 4.87(s,2H), 7.30-7.60(m,3H), 7.6-8.0(m,1H), 9.37(s,1H) |
| 5 | | 2.47(s,3H), 2.60(s,3H), 4.33(s,3H), 4.87(s,2H), 7.10-7.70(m,3H), 7.73-8.0(m,1H), 9.37(s,1H) |
| 7A | } isomeric | 1.57(d,3H), 2.50 and 2.53 (2s, totally 3H), |
| 7B | } mixture | 5.20(q,1H), 7.27-7.50(m,2H), 7.60-7.83(m,1H), 8.13-8.33(m,2H), 8.70-8.97(m,1H), 9.67(d,1H) |
| 8 | | 1.60(d,3H), 2.47(s,3H), 2.50(s,3H), 5.23(q,1H), 7.50(s,1H), 7.77(s,1H), 8.33(s,1H), 8.43(s,1H), 8.90(d,1H), 9.80(d,1H) |
| 10 | | 2.46(s,9H), 4.30(s,3H), 4.83(s,2H), 7.40-7.80 (m,3H), 9.50(d,1H) |
| 11 | | 2.43(s,6H), 2.47(s,3H), 4.30(s,3H), 4.97(s,2H), 7.20(s,2H), 7.40(d,1H), 9.50(d,1H) |
| 13 | | 2.43(s,3H), 2.50(s,3H), 2.63(s,3H), 2.70(s,3H), 4.90(s,2H), 7.50(s,1H), 7.70(s,1H), 8.60(s,1H), 9.47(s,1H) |

Incorporation of the new sulphenamides of the present invention in pharmaceutical preparations is exemplified by the following example.

EXAMPLE 80

Tablets

3-Methoxy-4,9,10-trimethyl-5-H-pyrido[1',2':4,5][1,2,4]thiadiazino[2,3-a]-benzimidazol-13-ium chloride (250 g), was mixed with 500 g lactose anhydrous
500 g microcrystalline cellulose
100 g crosslinked polyvinylpyrrolidone in a mixer. 5 g of magnesium stearate was admixed and the mixture was pressed into tablets each weighing 275 mg.

BIOLOGICAL TESTS

I. In Vitro Inhibition of Gastric H+,K+-ATPase

Hog gastric H+,K+-ATPase was purified according to Saccomani et al., Biochim. Biophys, Acta 465, 311-330, 1977. 10 μg of membrane protein (GI-fraction in the reference listed above) was incubated with 2 mmol/l of piperazine-N,N'-bis-(2-ethane sulfonic acid) buffer pH 7,4 and the test compound in concentrations $10^{-7}-10^{-4}$M in a final volume of 1 ml. (The test compound was dissolved in methanol. Aliquots of these stock solutions were diluted to a final methanol concentration below 1%, which on its own had no effect on the enzyme activities.) After 30 minutes of incubation, the remaining H+,K+-ATPase activity was determined, according to Wallmark et al., Biochim. Biophys. Acta, 728, 31-38, 1983. A dose-response curve was constructed and the concentration at half-maximal inhibition (IC$_{50}$) could be determined. When testing the isomeric mixture from Examples 1A and 1B and IC$_{50}$=6.10$^{-7}$M was obtained.

II. Inhibiting Effect in Vivo on Gastric Acid Secretion in Conscious Dog

Test Method

Chronic gastric fistula dogs were used. These dogs have been surgically provided with a gastric cannula in the stomach and a duodenal fistula used for direct intraduodenal administration of test compounds. Following a 4 weeks' recovery period after surgery, tests were performed once a week on each dog. Food and water were withdrawn 18 hours before each test.

The test compond was suspended in 0.5% Methocel ® (90 HG, 15.000, Dow Chem Corp.), the pH was immediately adjusted to about 4 by addition of hydrochloric acid and the suspension administered orally by using a stomach tube. After 1 hour gastric acid secretion was induced by continuous infusion of histamine at individual doses (400-600 nmol/kg, h), resulting in approx. 90% of maximal secretion of gastric acid. The gastric juice was collected by free flow from the gastric cannula in consecutive 30 minutes samples for 2 hours. The samples were titrated to pH 7.0 with 0.1M NaOH using a Radiometer automatic titrator and the acid output was calculated. The percent inhibition of acid secretion was calculated by comparing in each dog the acid output in the tests to the acid output in control tests when only the vehicle was given. The peak inhibitory effect for each compound was determined. When testing the isomeric mixture from Examples 1A and 1B at a concentration of 4 μmol/kg an inhibition of 40% was obtained.

III. In Vivo Cytoprotective Effect: Effect on Ethanol-Induced Gastric Lesions in the Rat Two groups of female Sprague-Dawley rats (190-220 g) were used, one for the test compound and one for the control experiment. Food, but not water, was removed 24 h before the experiments.

The animals in the test group were treated orally with the test compound dissolved in 0.01M HCl immediately before the test and the animals in the control group were given the vehicle (0.01M HCl) in a dose of 1 ml/kg.

Five or thirty minutes later the rats were given orally 1 ml of absolute ethanol (a standard agent for inducing gastric mucosal lesions).

Thirty minutes later the rats were killed by carbon dioxide asphyxiation, their stomachs dissected out and the gastric mucosae were examined for the presence of necrotic lesions. The total lengths of the lesions in the stomachs were measured in the test group and in the control group, in both cases treated five and thirty minutes before with ethanol.

When testing the isomeric mixture from Example 1A and 1B at a dose of 20 μmol/kg the total lengths of lesions in the stomachs were reduced to 5.3 cm (5 min) and 4.4 cm (30 min) compared to the lesions of the controls, which were 11.4 cm (5 min) and 10.4 cm (30 min). This indicates an ED$_{50}$-value below 20 μmol/kg.

The biological tests thus show that the compounds with the general formula IIIa both inhibit gastric acid secretion and have a gastrointestinal cytoprotecting effect.

We claim:

1. A compound of the formula

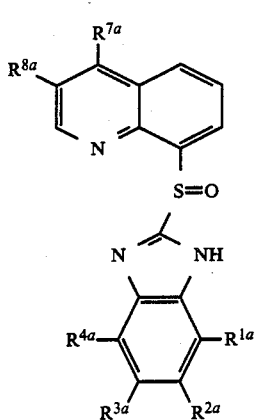

wherein
$R^{1a}$, $R^{2a}$, $R^{3a}$ and $R^{4a}$ are the same or different and are selected from the group consisting of
hydrogen,
alkyl of 1-7 carbon atoms,
alkoxy of 1-7 carbon atoms,
fluorine or chlorine substituted alkoxy of 1-7 carbon atoms,
halogen,
—CN,
—CF$_3$,
—NO$_2$,
—COR,
—COOR,
aryl of up to 10 carbon atoms, and
aryloxy of up to 10 carbon atoms, wherein R is alkyl of 1 to 7 carbon atoms, cycloalkyl or 3 to 10 carbon atoms, aryl of up to 10 carbon atoms or aralkyl of up to 10 carbon atoms in the aryl group and 1 to 7 carbon atoms in the alkyl group;
$R^{7a}$ is selected from the group consisting of
hydrogen,
alkyl of 1-7 carbon atoms,
alkoxy of 1-7 carbon atoms,
alkenyloxy of 2-5 carbon atoms, and
alkynyloxy of 2-5 carbon atoms; and
$R^{8a}$ is hydrogen or an alkyl group of 1-7 carbon atoms.

* * * * *